(12) United States Patent
Buynak et al.

(10) Patent No.: US 6,255,479 B1
(45) Date of Patent: Jul. 3, 2001

(54) PROCESS FOR THE PREPARATION OF α-OXOLACTAMS

(75) Inventors: John D. Buynak, Dallas, TX (US); Akireddy Srinivasa Rao, Waukegan, IL (US)

(73) Assignee: Research Corporation Technologies, Inc., Tucson, AZ (US)

( * ) Notice: Subject to any disclaimer, the term of this patent is extended or adjusted under 35 U.S.C. 154(b) by 0 days.

(21) Appl. No.: 09/222,519

(22) Filed: Dec. 29, 1998

Related U.S. Application Data

(60) Provisional application No. 60/068,927, filed on Dec. 29, 1997.

(51) Int. Cl.[7] ............... C07D 477/06; C07D 501/04; C07D 223/10; C07D 211/42; C07B 41/06

(52) U.S. Cl. .............. 540/215; 540/205; 540/229; 540/230; 540/301; 540/302; 540/310; 540/347; 540/507; 540/518; 540/526; 540/533; 546/137; 546/142; 546/155; 546/183; 546/243; 548/485; 548/513; 548/544

(58) Field of Search ............... 540/215, 229, 540/230, 301, 302, 310, 205, 347, 507, 518, 526, 533; 548/485, 513, 544; 546/137, 142, 155, 183, 243

(56) References Cited

U.S. PATENT DOCUMENTS

| | | | |
|---|---|---|---|
| 4,456,755 | * 6/1984 | Sheehan | 544/229 |
| 5,597,817 | 1/1997 | Buynak et al. | 514/200 |
| 5,629,306 | 5/1997 | Buynak et al. | 514/206 |
| 5,681,563 | 10/1997 | Buynak et al. | 424/114 |
| 5,760,027 | 6/1998 | Buynak et al. | 514/200 |

FOREIGN PATENT DOCUMENTS

| | | |
|---|---|---|
| 2708219 | 9/1977 | (DE) . |
| 0 050 805 | 5/1982 | (EP) . |
| 0 150 984 | 8/1985 | (EP) . |
| 0 367 606 | 5/1990 | (EP) . |
| 0 043 546 | 1/1992 | (EP) . |
| 98/24793 | 6/1998 | (WO) . |

OTHER PUBLICATIONS

Abd El–Nabi, H.A., "Novel Heterocycles: A convenient Synthesis of Pyrrolo [2,3–d]pyrazole; Cycloaddition reation of N–aryl(methyl)pyrrol–2,3–Diones to diazomethane and olefins", *Tetrahedron*, 53(5), 1813–1822, (Feb. 1997).

Arisawa, M., et al., "6–Acetylmethylenepenicillanic Acid (Ro 15–1903), A Potent β–Lactamase Inhibitor. I. Inhibition of Chromosomally and R–Factor–Mediated β–Lactamases", *The Journal of Antibiotics*, 35(11), 1578–1583, (Nov. 1982).

Bennett, I.S., et al., "6–(Substituted Methylene) Penems, Potent Broad Spectrum Inhibitors of Bacterial β–Lactamase. V. Chiral 1,2,3–Triazolyl Derivatives", *The Journal of Antibiotics*, 44(9), 969–978, (Sep. 1991).

Brenner, D.G., et al., "6–(Methoxymethylene) penicillanic Acid: Inactivator of RTEM β–Lactamase from *Escherichia coli*", *Biochemistry*, 23(24), 5839–5846, (Nov. 20, 1984).

Buynak, J.D., et al., "Synthesis and biological activity of 7–alkylidenecephems", *J. Med. Chem.*, 38, 1022–1034, (1995).

Buynak, J.D., et al., "Synthesis and mechanistic evaluation of 7–vinylidenecephem sulfones as β–lactamase inhibitors", *J. of Am. Chem. Soc.*, 116, 10955–10965, (1994).

Buynak, J.D., et al., "Synthesis of 6–vinylidenepenams", *The Journal of Organic Chemistry*, 58(6), 1325–1335, (Mar. 12, 1993).

(List continued on next page.)

Primary Examiner—Mark L. Berch
(74) Attorney, Agent, or Firm—Schwegman, Lundberg, Woessner & Kluth, P.A.

(57) ABSTRACT

A method for preparing an α-oxolactam comprising, reacting a corresponding α-diazolactam with an oxygen donor, in the presence of a transition metal catalyst, to yield the corresponding α-oxolactam.

18 Claims, 1 Drawing Sheet

5

6

7

OTHER PUBLICATIONS

Buynak, J.D., et al., "The Synthesis and Lactamase Inhibotory Activity of 6–(Carboxymethylene) Pencillins and 7–(Carboxymethylene) Cephalosporins", *Bioorganic & Medicinal Chemistry Letters*, 5 (14), 1513–1518, (1995).

Chen, Y.L., et al., "Synthesis of a Potent β–Lactamase Inhibitor–1,1–Dioxo–6–(2–Pyridyl) Methylenepenicillanic Acid and its Reaction with Sodium methoxide", *Tetrahedron Letters*, 27 (30), 3449–3452, (1986).

Hagiwara, D., et al., "An Efficient Synthesis of 6–Oxopenicillanic and 7–Oxocephalosporanic Acid Derivatives", *Journal of the Chemical Society Chemical Communications*, 11, 578–579, (Jun. 1, 1982).

Kant, J., et al., "Diastereoselective Addition of Grignard Reagents to Azetidine–2,3–dione: Synthesis of Novel Taxol Analogues", *Tetrahedron Letters*, 37 (36), 6495–6498, (Sep. 2, 1996).

Kollenz, G., et al., "Reactions of Cyclic Oxalyl Compounds—38. New Isoindigoide Dyes from Heterocyclic 2,3–Diones—Synthesis and Thermal Rearrangement", *Tetrahedron*, 52(15), 5427–5440, (Apr. 1996).

Martin, M.G., et al., "Epoxides as Alkene Protecting Groups. A Mild and Efficient Deoxygenation", *Tetrahedron Letters*, 25 (3), 251–254, (1984).

Palomo, C., et al., "New Synthesis of α–Amino Acid N–Carboxy Anhydrides through Baeyer–Villiger Oxidation of α–keto β–Lactams", *The Journal of Organic Chemistry*, 59 (11), 3123–3130, (Jun. 3, 1994).

van der Veen, J.M., et al., "Synthesis of Azetidine–2,3–diones (α–Keto β–Lactams) via 3–(Phenylthio)–2–azetidinones", *The Journal of Organic Chemistry*, 54 (24), 5758–5762, (Nov. 24, 1989).

Ursini, F., et al., "New Synthesis of 6–Oxopenicillanates by Ozonolysis of 6–Diazopenicillanates", *Synthesis*, 4, 363–364, (1992).

* cited by examiner

5

6

7

PROCESS FOR THE PREPARATION OF α-OXOLACTAMS

PRIORITY OF INVENTION

This application claims priority of invention under 35 U.S.C. §119(e) from U.S. Provisional Application No. 60/068,927, filed Dec. 29, 1997.

BACKGROUND OF THE INVENTION

α-Oxolactams are useful synthons for preparing a variety of natural products and biologically active compounds (for example see A. Hisham *Tetrahedron*, 1997, 53, no. 5, 1813–1822). They can also be used to prepare synthetically useful α-substituted-ω-amino carboxylic acids, and to prepare a variety of isoindigoide dyes (G. Kollenz, et al. *Tetrahedron*, 1996, 52, no. 15, 5427–5440).

α-Oxo-β-lactams, such as 6-oxopenams, 7-oxocephems and 6-oxopenems, are also useful for preparing α-alkylidene-β-lactams and α-vinylidene-β-lactams, both important classes of β-lactamase inhibitors (U.S. Pat. No. 5,597,817, issued Jan. 29, 1997 ("817"); U.S. Pat. No. 5,629,306, issued May 13, 1997 ("306"); Buynak et al., *J. Org. Chem.*, 1993, 58, 1325.; Buynak et al., *J. Am. Chem. Soc.*, 1994, 116, 10955; Buynak et al., *J. Med. Chem.*, 1995, 38, 1022; Buynak et al., *Bioorg. Med. Chem. Lett.*, 1995, 5, 1513; Arisawa et al., *J. Antibiot.*, 1982, 35, 1578; Brenner et al., *Biochemistry*, 1984, 23, 5839; Chen et al., *Tetrahedron Lett.*, 1986, 27, 3449; Bennet et al., *J. Antibiot.*, 1991, 44, 969.

α-Oxo-β-lactams have also been used to prepare cytotoxic analogs of paclitaxel (J. Kant et al. *Tetrahedron Letters*, 1996, 37, 6495–6498); and to prepare α-aminoacid N-carboxy anhydrides and their corresponding α-amino acid derivatives (C. Palomo *J. Org. Chem.*, 1994, 59, 3123–3130).

J. M. van der Veen et al. *J. Org. Chem.*, 1989, 54, 5758–5762 disclose the preparation of specific α-oxo-β-lactams by hydrolysis of the corresponding α-chloro-α-phenylthio-β-lactams, which are prepared by the treatment of α-phenylthio-β-lactams with N-chlorosuccinimide. C. Palomo et al. *J. Org. Chem*, 1994, 59, 3123–3130, disclose the preparation of specific α-oxo-β-lactams by oxidation of the corresponding α-hydroxy-β-lactams using $Me_2SBr_2$—$NEt_3$, $CrO_3$— pyridine, or $DMSO-P_2O_5$. U.S. patents '817 and '306 disclose the preparation of specific α-oxo-β-lactams by treatment of the corresponding α-amino-β-lactams with trifluoromethanesulfonic anhydride and triethylamine, followed by aqueous acid.

Existing methods for preparing α-oxolactams are limited because they require the use of toxic or corrosive reagents, produce hazardous side products, require starting materials that are difficult or expensive to prepare, or yield products that can not be easily isolated or purified. Additionally, existing methods can not conveniently be preformed to yield products on a commercially useful (e.g. kilogram) scale. Therefore, there is a need for improved methods for preparing α-oxolactams, which overcome one or more of the limitations of the existing synthetic methods.

SUMMARY OF THE INVENTION

The present invention provides a method comprising reacting an α-diazolactam with an oxygen donor, in the presence of a transition metal catalyst to yield the corresponding α-oxolactam. The method utilizes non-toxic reagents, does not produce hazardous side products, and yields a product that can be easily isolated. Additionally, the method is mild and selective, and allows for the preparation of the α-oxolactam functionality in the presence of a wide variety of other functional groups.

The method may also further comprise the step of preparing the α-diazolactam from a corresponding α-aminolactam by diazotization.

DETAILED DESCRIPTION OF THE INVENTION

Oxygen Donors

Figure 1:
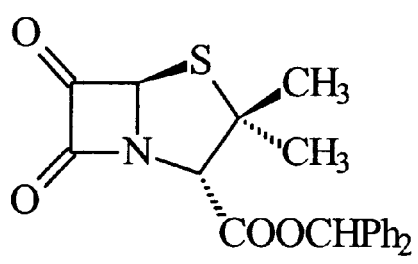
FIG. 1 shows the α-oxo-β-lactams prepared in Example 1, Example 2, and Example 3.
Figure 1:
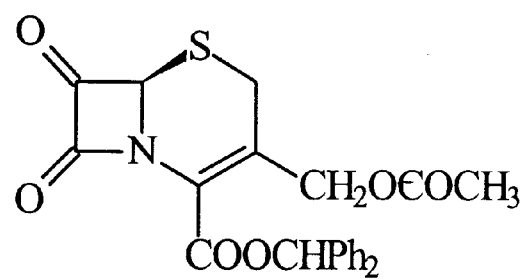
Figure 1:
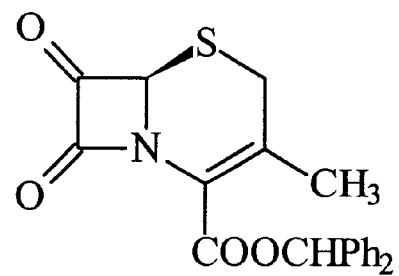

The method of the instant invention may be practiced using any suitable oxygen donor. Preferably, the oxygen donor is an epoxide. For example, the method may be carried out using an epoxide of formula (I):

(I)

wherein a) $R_1$, $R_2$, $R_3$, and $R_4$ are each independently hydrogen, or $(C_1-C_{10})$alkyl; or b) $R_1$ and $R_3$, or $R_1$ and $R_2$, together with the carbon atoms to which they are attached form a five to eight membered carbocyclic ring; or c) $R_2$ and $R_4$, or $R_3$ and $R_4$, together with the carbon atoms to which they are attached form a five to eight membered carbocyclic ring; or d) any possible combination of a), b), and c).

The nature of the organic epoxide is not critical to the practice of the present method, so long as it is compatible with the reactants to which it is exposed. Preferably, the epoxide is ethylene oxide, propylene oxide, 1-butylene oxide, 2-butylene oxide, isobutylene oxide, 1-pentene oxide, 2-pentene oxide, 1-isopentene oxide, 2-isopentene oxide, 3-isopentene oxide, 1-hexene oxide, 2-hexene oxide, 3-hexene oxide, cyclopentene oxide, cyclohexene oxide, cycloheptene oxide, or cyclooctene oxide.

The method may also be carried out using the epoxides described in M. G. Martin and B. Ganem, *Tetrahedron Letters*, 1984, 25, 251–254, or using epoxides similar thereto.

Transition Metal Catalyst

The invention may be practiced using any suitable transition metal catalyst, such as an inorganic or organic salt of a group VIII, VIIB, IB, or IIB metal. The catalyst may conveniently comprise rhodium (II), rhenium (V), rhenium (VII), copper (I), or copper (II).

Suitable catalysts comprising copper are well known in the art and include the copper catalysts disclosed to be useful for carrying out intramolecular insertion reactions by S. D. Burke, and P. A. Grieco, *Org. React.* 26, 361–474 (1979). Specific copper catalysts include copper (II) acetylacetonate, copper (I) iodide, copper (I) trifluoromethanesulfonate, copper (II) trifluoromethanesulfonate, copper (II) sulfate, copper (I) oxide, copper (II) oxide, copper powder, copper (I) bromide, and copper (I) chloride.

In a preferred embodiment of the invention, the catalyst comprises rhodium (II). More preferably, the catalyst comprises a binuclear rhodium (II) carboxylate salt, for example, $Rh_2(OAc)_4$, rhodium octanoate dimer, or rhodium pivalate dimer.

In another preferred embodiment of the invention, the catalyst comprises rhenium (V) or rhenium (VII). More preferably, the catalyst comprises $MeReO_3$ or $ReOCl_3(PPh_3)_2$ (B. E. Ledford and E. M. Carreira *Tetrahedron Letters*, 1997, 38, 8125–8128).

α-Oxolactams

Because of the mild reaction conditions involved, the method of the invention is generally useful for preparing α-oxolactams (e.g. α-oxo-β-lactams, α-oxo-γ-lactams and α-oxo-δ-lactams).

Specifically, the method of the invention is useful for preparing α-oxo-β-lactams of formula II:

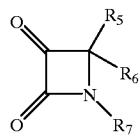

(II)

wherein $R_5$, $R_6$ and $R_7$, either alone or in any combination, are organic moieties compatible with the reaction conditions of the method of the invention.

The method of the invention is also specifically useful for preparing an α-oxo-β-lactam of formula (II) wherein $R_5$, $R_6$ and $R_7$ are each individually hydrogen, $(C_1-C_{10})$alkyl, aryl, heteroaryl, or any combination thereof.

The method of the invention is also specifically useful for preparing an α-oxo-β-lactam of formula II wherein $R_5$, $R_6$ and $R_7$ together with the α-oxo-β-lactam ring to which they are attached, form an α-oxopenam, α-oxopenem, α-oxocarbapenem, α-oxocephem, α-oxocarbacephem or α-(oxo)oxacephem ring system, or an intermediate useful (or subsequently used) for preparing such a ring system. Compounds comprising such a ring system can be used for preparing antibiotics or β-lactamase inhibitors, such as those disclosed in U.S. patents '817 and '306 cited hereinabove, and those disclosed by I. Heinze-Krauss et al. *J. Med. Chem.* 1996, 39, 1864–1871. In particular, the method is useful for preparing 6-oxopenams, 7-oxocephems and 6-oxopenems, because it allows for the introduction of the α-oxo-substituent in the presence of the reactive sulfide sulfur of these ring systems.

The method of the invention is also specifically useful for preparing an α-oxo-β-lactam intermediate of formula II wherein $R_5$ is phenyl, $R_6$ is hydrogen and $R_7$ is tert-butyldimethylsilyl. This compound is a useful intermediate for preparing taxol analogs (J. Kant *Tetrahedron Letters*, 1996, 37, 6495–6498).

The method of the invention is also specifically useful for preparing α-oxo-β-lactam intermediates of formula II wherein $R_5$ is hydrogen, phenyl, methyl, (tert-butyldiphenylsilyloxy) methyl, (1-tert-butoxycarbonylamino)ethyl, or α-(tert-butyldimethylsilyloxy)benzyl; $R_6$ is hydrogen; and $R_7$ is 4-methoxyphenyl or benzyl. These compounds are useful for preparing α-aminoacid N-carboxy anhydrides and their corresponding α-amino acid derivatives (C. Palomo *J. Org. Chem.*, 1994, 59, 3123–3130).

The method of the invention is also specifically useful for preparing α-oxo-β-lactam intermediates of formula II wherein $R_5$ is phenyl, optionally substituted with one or two substituents independently selected from the group consisting of halogen, $(C_1-C_4)$alkyl, $(C_1-C_3)$alkoxy, hydroxyl, and cyano; $R_6$ is hydrogen; and $R_7$ is $(C_1-C_4)$alkyl, cyclopentyl, cyclohexyl, 1-naphthylmethyl, 1-phenethyl, 1-carboxy-2-phenethyl, phenyl, benzyl, or 3-[$(C_1-C_4)$alkoxycarbonyl]-1-[$(C_1-C_4)$alkoxy-carbonyl]propyl, wherein any phenyl or benzyl may optionally be substituted on the phenyl ring with one or two substituents independently selected from the group consisting of halogen, $(C_1-C_4)$alkyl, $(C_1-C_3)$alkoxy, dimethylamino, carboxy, dichloroacetyl and trifluoromethyl. These compounds are useful for preparing 2-azetidinone blood aggregation inhibitors (Y. Kawashima Japanese Patent Application Publication Number JP 01135763; and European Patent Application Publication Number 264231).

The method of the invention is also specifically useful for preparing an α-oxo-β-lactam of formula (II) wherein $R_5$ and $R_6$ are each hydrogen; and $R_7$ is phenyl. This compound is a useful intermediate for preparing antibiotics (I. Heinze-Krauss et al. *J. Med. Chem.* 1996, 39, 1864–1871).

The method of the invention is also specifically useful for preparing an α-oxo-β-lactam of formula (II) wherein $R_5$ is phenyl, 4-methoxyphenyl, 2-bromophenyl, or styryl; $R_6$ is hydrogen; and $R_7$ is 4-methoxyphenyl. These compounds are useful for preparing α-allyl-β-lactams which can be used to prepare a variety of heterocyclic compounds including pyrrolidine and piperidine alkaloids (M. Jayaranam et al. *Tetrahedron Letters*, 1997, 38, 709–712; A. K. Bose et al. *Tetrahedron Letters*, 1986, 27, 5955).

The method of the invention may also specifically be useful for preparing the aldose reductase inhibitor 1-benzyl-3-hydroxy-2(5H)-oxopyrrole-4-carboxylate as well as other biologically active compounds and intermediates disclosed by B. L. Mylari, *J. Med. Chem.*, 1991, 34, 1011–1018.

Preferably, the α-oxo-β-lactam prepared by the method of the invention is a compound of formula (III):

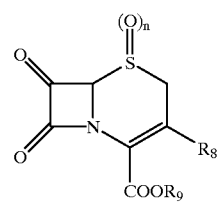

(III)

wherein
n is 0, 1, or 2;
$R_8$ is hydrogen, carboxy, chloro, fluoro, trifluoromethyl, formyl, or —$CH_2M$;
M is
  hydrogen;
  halo;
  hydroxy;
  $(C_1-C_{10})$alkoxy;
  aryloxy;
  aryl$(C_1-C_{10})$alkoxy;
  mercapto;
  mercapto substituted with $(C_1-C_{10})$alkyl, aryl, or aryl $(C_1-C_{10})$alkyl;
  $(C_2-C_{10})$alkanoylthio;
  $(C_2-C_{10})$alkanoyloxy;
  $(C_2-C_{10})$carbamoyloxy;
  $(C_2-C_{10})$alkanoyloxy or $(C_2-C_{10})$carbamoyloxy, substituted with one or more carboxy, aminophenyl, phenyl, $(C_1-C_6)$alkyl, chloro, bromo or fluoro; or
  $N(R)_2$, wherein each R is independently selected from hydrogen, $(C_1-C_{10})$alkyl, or $(C_1-C_{10})$alkanoyl; and
$R_9$ is hydrogen, $(C_1-C_{10})$alkyl, $(C_3-C_8)$cycloalkyl, $C_3-C_8)$cycloalkyl$(C_1-C_{10})$alkyl, aryl, aryl$(C_1-C_{10})$ alkyl, or diaryl$(C_1-C_{10})$alkyl;

or a salt thereof.

In another preferred embodiment of the invention, the α-oxo-β-lactam prepared by the method of the invention is a compound of formula (IV):

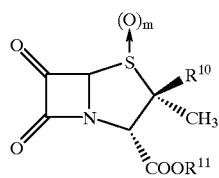

(IV)

wherein
R$^{10}$ is (C$_3$–C$_{10}$)alkyl, (C$_2$–C$_{10}$)alkenyl, (C$_2$–C$_{10}$)alkynyl, (C$_1$–C$_{10}$)alkanoyl, (C$_3$–C$_8$)cycloalkyl, aryl, heteroaryl, aryl(C$_1$–C$_{10}$)alkyl, heteroaryl(C$_1$–C$_{10}$)alkyl, or —CH$_2$R$_a$, wherein R$_a$ is halo, cyano, cyanato, —OR$_b$, —NR$_c$R$_d$, azido, —SR$_e$, or (C$_3$–C$_8$)cycloalkyl;
R$^{11}$ is hydrogen, (C$_1$–C$_{10}$)alkyl, (C$_3$–C$_8$)cycloalkyl, (C$_2$–C$_{10}$)alkenyl, (C$_2$–C$_{10}$)alkynyl, aryl, or heteroaryl;
m is 0, 1, or 2;
R$_b$ is hydrogen, (C$_1$–C$_{10}$)alkyl, (C$_3$–C$_8$)cycloalkyl, (C$_2$–C$_{10}$)alkenyl, (C$_2$–C$_{10}$)alkynyl, —C(=O)N(R$_g$)$_2$, aryl, heteroaryl, arylcarbonyl, heteroarylcarbonyl, or (C$_1$–C$_{10}$)alkanoyl, wherein each R$_g$ is independently hydrogen, (C$_1$–C$_{10}$)alkyl, aryl, benzyl, phenethyl, or heteroaryl;
each R$_c$ or R$_d$ is independently hydrogen, (C$_1$–C$_{10}$)alkyl, (C$_3$–C$_8$)cycloalkyl, (C$_2$–C$_{10}$)alkenyl, (C$_2$–C$_{10}$)alkynyl, (C$_1$–C$_{10}$)alkanoyl, —C(=O)N(R$_h$)$_2$, aryl, benzyl, phenethyl, heteroaryl oxazolidinyl, isoxazolidinyl, or morpholinyl; wherein each R$_h$ is independently hydrogen, (C$_1$–C$_{10}$)alkyl, aryl, benzyl, phenethyl, or heteroaryl; or R$_c$ and R$_d$ together with the nitrogen to which they are attached are triazolyl, imidazolyl, oxazolidinyl, isoxazolidinyl, pyrrolyl, morpholino, piperidino, pyrrolidino, pyrazolyl, indolyl, or tetrazolyl; and
R$_e$ is hydrogen, (C$_1$–C$_{10}$)alkyl, (C$_3$–C$_8$)cycloalkyl, (C$_2$–C$_{10}$)alkenyl, (C$_2$–C$_{10}$)alkynyl, cyano, aryl, benzyl, phenethyl, heteroaryl, oxazolidinyl, isoxazolidinyl, or morpholinyl;
wherein any (C$_1$–C$_{10}$)alkyl, (C$_3$–C$_8$)cycloalkyl, (C$_2$–C$_{10}$)alkenyl, (C$_2$–C$_{10}$)alkynyl, (C$_1$–C$_{10}$)alkanoyl, aryl, benzyl, phenethyl, heteroaryl, arylcarbonyl, heteroarylcarbonyl, oxazolidinyl, isoxazolidinyl, or morpholinyl of R$^{10}$, R$^{11}$, R$_a$–R$_e$, or R$_g$–R$_h$, may optionally be substituted with 1, 2, or 3 Z; and each Z is independently halo, nitro, cyano, hydroxy, (C$_1$–C$_{10}$)alkyl, (C$_3$–C$_8$)cycloalkyl, (C$_1$–C$_{10}$)alkoxy, (C$_1$–C$_{10}$)alkanoyl, (C$_2$–C$_{10}$)alkanoyloxy, trifluoromethyl, aryl, aryloxy, heteroaryl, or —SR$_f$, wherein R$_f$ is hydrogen, (C$_1$–C$_{10}$)alkyl, (C$_3$–C$_8$)cycloalkyl, aryl, benzyl, phenethyl, or heteroaryl;
and further wherein any aryl, aryloxy, heteroaryl, benzyl, or phenethyl of Z may optionally be substituted with 1, 2, or 3 substituents independently selected from the group consisting of halo, nitro, cyano, hydroxy, (C$_1$–C$_{10}$)alkyl, (C$_3$–C$_8$)cycloalkyl, (C$_1$–C$_{10}$)alkoxy, (C$_1$–C$_{10}$)alkanoyl, (C$_2$–C$_{10}$)alkanoyloxy, benzyloxy, 4-methoxybenzyloxy, and trifluoromethyl; or a salt thereof.

The invention also provides novel compounds of formulae III and IV.

The following definitions apply herein unless otherwise described: halo is fluoro, chloro, bromo, or iodo. Alkyl, alkoxy, alkenyl, alkynyl etc. denote both straight and branched groups, but reference to an individual radical such as "propyl" embraces only the straight chain radical, a branched chain isomer such as "isopropyl" being specifically referred to. Aryl denotes a phenyl radical or an ortho-fused bicyclic carbocyclic radical having about nine to ten ring atoms in which at least one ring is aromatic. Heteroaryl encompasses a radical attached via a ring carbon of a monocyclic aromatic ring containing five or six ring atoms consisting of carbon and one to four heteroatoms each selected from the group consisting of non-peroxide oxygen, sulfur, and N(X) wherein X is absent or is H, O, (C$_1$–C$_4$) alkyl, phenyl or benzyl, as well as a radical of an ortho-fused bicyclic heterocycle of about eight to ten ring atoms derived therefrom, particularly a benz-derivative or one derived by fusing a propylene, trimethylene, or tetramethylene diradical thereto.

It will be appreciated by those skilled in the art that c&-oxolactams having one or more chiral centers may exist in and be prepared in optically active and racemic forms. The present invention provides a method which is generally useful for preparing any racemic, optically-active, or stereoisomeric form of a given α-oxolactam.

Specifically, (C$_1$–C$_{10}$)alkyl can be methyl, ethyl, propyl, isopropyl, butyl, iso-butyl, sec-butyl, pentyl, 3-pentyl, hexyl, heptyl, octyl, nonyl or decyl; (C$_3$–C$_8$)cycloalkyl can be cyclopropyl, cyclobutyl, cyclopentyl, cyclohexyl, cycloheptyl, or cyclooctyl; (C$_1$–C$_{10}$)alkoxy can be methoxy, ethoxy, propoxy, isopropoxy, butoxy, iso-butoxy, sec-butoxy, pentoxy, 3-pentoxy, hexyloxy, heptyloxy, octyloxy, nonyloxy, or decyloxy; (C$_2$–C$_{10}$)alkenyl can be vinyl, allyl, 1-propenyl, 2-propenyl, 1-butenyl, 2-butenyl, 3-butenyl, 1,-pentenyl, 2-pentenyl, 3-pentenyl, 4-pentenyl, 1-hexenyl, 2-hexenyl, 3-hexenyl, 4-hexenyl, 5-hexenyl, 1-heptenyl, 2-heptenyl, 3-heptenyl, 4-heptenyl, 5-heptenyl, 6-heptenyl, 1-octenyl, 2-octenyl, 3-octenyl, 4-octenyl, 5-octenyl, 6-octenyl, 7-octenyl, 1-nonenyl, 2-nonenyl, 3-nonenyl, 4-nonenyl, 5-nonenyl, 6-nonenyl, 7-nonenyl, 8-nonenyl, 1-decenyl, 2-decenyl, 3-decenyl, 4-decenyl, 5-decenyl, 6-decenyl, 7-decenyl, 8-decenyl, or 9-decenyl; (C$_2$–C$_{10}$) alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, 1-heptynyl, 2-heptynyl, 3-heptynyl, 4-heptynyl, 5-heptynyl, 6-heptynyl, 1-octynyl, 2-octynyl, 3-octynyl, 4-octynyl, 5-octynyl, 6-octynyl, 7-octynyl, 1-nonylyl, 2-nonynyl, 3-nonynyl, 4-nonynyl, 5-nonynyl, 6-nonynyl, 7-nonynyl, 8-nonynyl, 1-decynyl, 2-decynyl, 3-decynyl, 4-decynyl, 5-decynyl, 6-decynyl, 7-decynyl, 8-decynyl, or 9-decynyl; (C$_1$–C$_{10}$)alkanoyl can be acetyl, propanoyl, butanoyl, isobutanoyl, pentanoyl, hexanoyl, heptanoyl, octanoyl, nonanoyl, or decanoyl; and (C$_2$–C$_{10}$)alkanoyloxy can be acetoxy, propanoyloxy, butanoyloxy, isobutanoyloxy, pentanoyloxy, hexanoyloxy, heptanoyloxy,

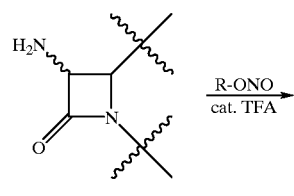

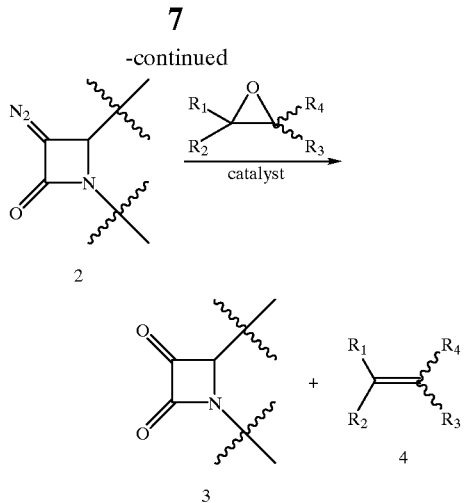

octanoyloxy, nonanoyloxy, or decanoyloxy. Likewise, aryl can be phenyl, indenyl, or naphthyl. Heteroaryl can be furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide), thiadiazolyl, thiatriazolyl, oxadiazolyl, or quinolyl (or its N-oxide).

Specific and preferred values given herein for radicals, substituents, and ranges, are for illustration only and they do not exclude other defined values or other values within defined ranges for the radicals and substituents.

Starting Materials

The requisite α-diazolactam starting materials can be prepared from a corresponding α-aminolactams by diazotization using techniques which are well known to the art. The diazotization of an α-amino-β-lactam 1, is illustrated in Scheme I.

Scheme I

Treatment of amine 1 with isopropyl or iso amyl nitrite (R-ONO) in the presence of trifluoroacetic acid gives α-diazo-β-lactam 2. Suitable conditions for diazotizing amines are well known in the art; see for example J. March *Advanced Organic Chemistry*, John Wiley & Sons, 4ed., 1992; or H. O. House *Modern Synthetic Reactions*, W. A. Benjamin, Inc., 2ed., 1972. Diazo compound 2 can be treated with an epoxide in the presence of a transition metal catalyst to yield α-oxo-β-lactam 3 and an olefin 4.

Salts

In cases where the α-oxolactam product (such as for example a compound of formula III or IV) is sufficiently basic or acidic to form a stable acid or base salt, the invention may further comprise the preparation of such a salt. Examples of acceptable salts are organic acid addition salts formed with acids which form an acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Salts may be obtained using standard procedures well known in the art, for example by reacting a sufficiently basic compound such as an amine with a suitable acid affording an acceptable anion. Alkali metal (for example, sodium, potassium or lithium) or alkaline earth metal (for example calcium) salts of carboxylic acids can also be made.

Summary

The invention provides a method for the synthesis of an α-oxolactam. It allows for the selective oxidation of an α-diazolactam to the corresponding α-oxolactam in the presence of other easily oxidizable groups. The invention also provides a method that can conveniently and cost effectively yield α-oxolactams on a commercial scale.

The invention will now be illustrated by the following non-limiting Examples.

EXAMPLE 1

Benzhydryl 6-oxopenicillanate

To a solution of benzhydryl 6-aminopenicillanate (2 g, 5.23 mmol) in ethyl acetate (20 mL) were added isopropyl nitrite (1.8 mL, 7.85 mmol, 40% solution in $CH_2Cl_2$) and trifluoroacetic acid (18 mg, 0.16 mmol) and the reaction was allowed to stir for 1 hour at room temperature. The reaction mixture was concentrated under reduced pressure and redissolved in benzene (15 mL). To this solution was added propylene oxide (30 g, 0.52 mol) followed by rhodium octanoate dimer (5 mg) and the reaction was stirred for 15 minutes (until evolution of nitrogen ceases). Volatiles were removed to yield the title compound (5, FIG. 1) (2 g, quantitative, 95% pure). IR ($CHCl_3$): 1820, 1775, 1730 $cm^{-1}$; $^1H$ NMR ($CDCl_3$): δ 7.38 (10H, bs), 7.00 (1H, s), 5.83 (1H, s), 4.91 (1H, s), 1.56 (3H, s), 1.36 (3H, s); $^{13}C$ NMR ($CDCl_3$): δ 190.4 (s), 168.0 (s), 165.8 (s), 139.1 (s), 138.6 (s), 128.5, 128.2, 127.6, 127.4, 127.1, 126.8, 126.5, 78.8 (d), 76.8 (d), 71.5 (d), 64.2 (s), 34.1 (q), 24.7 (q).

The starting material, benzhydryl 6-aminopenicillanate, can be readily prepared from 6-aminopenicillinic acid, which is available from Aldrich Chemical Company, Inc. Milwaukee, Wis., USA.

EXAMPLE 2

Benzhydryl 7-oxocephalosporanate

To a solution of benzhydryl 7-aminocephalosporanate (0.5 g, 1.146 mmol) in ethyl acetate (5 mL) were added isopropyl nitrite (0.38 mL, 1.71 mmol, 40% solution in $CH_2Cl_2$) and trifluoroacetic acid (6.5 mg, 0.05 mmol) and the reaction was allowed to stir for 1 hour at room temperature. The reaction mixture was concentrated under reduced pressure and redissolved in benzene (5 mL). To this solution was added propylene oxide (6.7 g, 0.114 mol) followed by rhodium octanoate dimer (2 mg) and the reaction was stirred for 15 minutes (until evolution of nitrogen ceases). Volatiles were removed to produce the title compound (6, FIG. 1) (0.5 g, quantitative, 90% pure). IR ($CHCl_3$) 3005, 1830, 1790, 1740 $cm^{-1}$; $^1H$ NMR ($CDCl_3$) δ 7.39 (10H, m), 7.05 (1H, s), 5.32 (1H, s), 5.07 (1H, d, A of ABq, J=13.9 Hz), 4.85 (1H, d, B of ABq, J=14.0 Hz), 3.64 (1H, d, A of ABq, J=18.5 Hz), 3.44 (1H, d, B of ABq, J=18.6 Hz), 2.05 (3H, s); $^{13}C$ NMR ($CDCl_3$) δ 188.4 (s), 170.3 (s), 160.1 (s), 158.7 (s), 138.8 (s), 138.6 (s), 128.4, 128.2, 128.1, 127.7, 126.9, 126.2, 80.1 (d), 65.8 (d), 62.6 (t), 27.7 (t), 20.4 (q).

The starting material benzhydryl 7-aminocephalosporanate can be readily prepared from 7-aminocephalosporanic acid, which is available from Aldrich Chemical Company, Inc. Milwaukee, Wis., USA.

EXAMPLE 3

Benzhydryl 7-oxo-3'-(desacetoxy)cephalosporanate

To a solution of benzhydryl 7-amino-3'-desacetoxycephalosporanate (15 g, 39.47 mmol) in ethyl acetate (300 mL) were added isopropyl nitrite (13.26 mL, 59.21 mmol, 40% solution in $CH_2Cl_2$) and trifluoroacetic acid (0.134 g, 1.184 mmol) and the reaction was stirred for 1 hour at room temperature, concentrated under reduced pressure, and redissolved in benzene (75 mL). Propylene oxide (150 mL) oxide was added, followed by rhodium octanoate dimer (100 mg) and the reacrion was stirred for 15 minutes (until evolution of nitrogen gas ceased). Volatiles were removed under reduced pressure to give the title compound in quantitative yield (15 g,>90% purity); $^1$H NMR (CDCl$_3$) δ 7.97–7.25 (m, 10H), 6.99 (s, 1H), 5.29 (s, 1H), 3.47 (d, J=17.86 Hz, 1H), 3.29 (d, J=17.86 Hz, 1H), 2.18 (s, 3H).

The starting material benzhydryl 7-amino-3'-desacetoxycephalosporanate can be readily prepared from 7-amino-3'-desacetoxycephalosporanic acid, which is available from Gist-brocades BV, a division of Gist-brocades international, Holland.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A method for preparing an α-oxolactam comprising reacting a corresponding α-diazolactam with an epoxide, in the presence of a transition metal catalyst, to yield the α-oxolactam.

2. The method of claim 1 further comprising, first preparing the α-diazolactam, by diazotizing a corresponding α-aminolactam.

3. The method of claim 1, wherein the epoxide is ethylene oxide, propylene oxide, 1-buylene oxide, 2-buylene oxide, isobutylene oxide, 1-pentene oxide, 2-pentene oxide 1-isopentene oxide, 2-isopentene oxide, 3-isopentene oxide, 1-hexene oxide, 2-hexene oxide, 3-hexene oxide, cyclopentene oxide, cyclohexene oxide, cycloheptene oxide, or cyclooctene oxide.

4. The method of claim 1, wherein the catalyst comprises rhodium (II), copper (I), copper (II), rhenium (V), or rhenium (VII).

5. The method of claim 1, wherein the catalyst comprises rhodium (II).

6. The method of claim 5, wherein the catalyst is Rh$_2$(OAc)$_4$, rhodium octanoate dimer, or rhodium pivalate dimer.

7. The method of claim 1 wherein the catalyst comprises rhenium (V) or rhenium (VII).

8. The method of claim 1 wherein the catalyst comprises CH$_3$ReO$_3$ or ReOCl$_3$(PPh$_3$)$_2$.

9. The method of claim 1 wherein the α-oxolactam is a α-oxo-β-lactam, α-oxo-γ-lactam, or an α-oxo-δ-lactam.

10. The method of claim 1 wherein the α-oxolactam is a α-oxo-β-lactam.

11. A method for preparing an α-oxo-β-lactam comprising reacting a corresponding α-diazo-β-lactam with an epoxide in the presence of a catalyst comprising rhodium (II), copper (I), copper (II), rhenium (VII), or rhenium (V).

12. The method of claim 11 wherein the catalyst comprises rhodium (II).

13. The method of claim 1, wherein the α-oxolactam is a compound of formula (III):

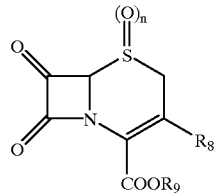

(III)

wherein
n is 0, 1, or 2;
R$_8$ is carboxy, chloro, fluoro, trifluoromethyl, formyl, or —CH$_2$M;
M is
hydrogen;
halo;
hydroxy;
(C$_1$–C$_{10}$)alkoxy;
aryloxy;
aryl(C$_1$–C$_{10}$)alkoxy;
mercapto;
mercapto substituted with (C$_1$–C$_{10}$)alkyl, aryl, or aryl (C$_1$–C$_{10}$)alkyl;
(C$_2$–C$_{10}$)alkanoylthio;
(C$_2$–C$_{10}$)alkanoyloxy;
(C$_2$–C$_{10}$)carbamoyloxy;
(C$_2$–C$_{10}$)alkanoyloxy or (C$_2$–C$_{10}$)carbamoyloxy, substituted with one or more carboxy, aminophenyl, phenyl, (C$_1$–C$_6$)alkyl, chloro, bromo or fluoro; or
N(R)$_2$, wherein each R is independently selected from hydrogen, (C$_1$–C$_{10}$)alkyl, or (C$_1$–C$_{10}$)alkanoyl; and
R$_9$ is hydrogen, (C$_1$–C$_{10}$)alkyl, (C$_3$–C$_8$)cycloalkyl, C$_3$–C$_8$)cycloalkyl(C$_1$–C$_{10}$)alkyl, aryl, aryl(C$_1$–C$_{10}$)alkyl, or diaryl(C$_1$–C$_{10}$)alkyl;
or a salt thereof.

14. The method of claim 13 wherein R$_8$ is acetoxymethyl.

15. The method of claim 1, wherein the α-oxo-lactam is a compound of formula (IV):

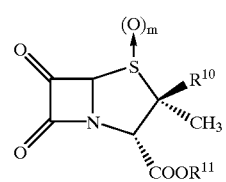

(IV)

wherein
R$^{10}$ is (C$_3$–C$_{10}$)alkyl, (C$_2$–C$_{10}$)alkenyl, (C$_2$–C$_{10}$)alkynyl, (C$_1$–C$_{10}$)alkanoyl, (C$_3$–C$_8$)cycloalkyl, aryl, heteroaryl, aryl(C$_1$–C$_{10}$)alkyl, heteroaryl(C$_1$–C$_{10}$)alkyl, or —CH$_2$R$_a$, wherein R$_a$ is halo, cyano, cyanato, —OR$_b$, —NR$_c$R$_d$, azido, —SR$_e$, or (C$_3$–C$_8$)cycloalkyl;
R$^{11}$ is hydrogen, (C$_1$–C$_{10}$)alkyl, (C$_3$–C$_8$)cycloalkyl, (C$_2$–C$_{10}$)alkenyl, (C$_2$–C$_{10}$)alkynyl, aryl, or heteroaryl;
m is 0, 1, or 2;
R$_b$ is hydrogen, (C$_1$–C$_{10}$)alkyl, (C$_3$–C$_8$)cycloalkyl, (C$_2$–C$_{10}$)alkenyl, (C$_2$–C$_{10}$)alkynyl, —C(=O)N(R$_g$)$_2$, aryl, heteroaryl, arylcarbonyl, heteroarylcarbonyl, or (C$_1$–C$_{10}$)alkanoyl, wherein each R$_g$ is independently hydrogen, (C$_1$–C$_{10}$)alkyl, aryl, benzyl, phenethyl, or heteroaryl;

each $R_c$ or $R_d$ is independently hydrogen, $(C_1-C_{10})$alkyl, $(C_3-C_8)$cycloalkyl, $(C_2-C_{10})$alkenyl, $(C_2-C_{10})$alkynyl, $(C_1-C_{10})$alkanoyl, —C(=O)N($R_h$)$_2$, aryl, benzyl, phenethyl, heteroaryl oxazolidinyl, isoxazolidinyl, or morpholinyl; wherein each $R_h$ is independently hydrogen, $(C_1-C_{10})$alkyl, aryl, benzyl, phenethyl, or heteroaryl; or $R_c$ and $R_d$ together with the nitrogen to which they are attached are triazolyl, imidazolyl, oxazolidinyl, isoxazolidinyl, pyrrolyl, morpholino, piperidino, pyrrolidino, pyrazolyl, indolyl, or tetrazolyl; and $R_e$ is hydrogen, $(C_1-C_{10})$alkyl, $(C_3-C_8)$cycloalkyl, $(C_2-C_{10})$alkenyl, $(C_2-C_{10})$alkynyl, cyano, aryl, benzyl, phenethyl, heteroaryl, oxazolidinyl, isoxazolidinyl, or morpholinyl;

wherein any $(C_1-C_{10})$alkyl, $(C_3-C_8)$cycloalkyl, $(C_2-C_{10})$alkenyl, $(C_2-C_{10})$alkynyl, $(C_1-C_{10})$alkanoyl, aryl, benzyl, phenethyl, heteroaryl, arylcarbonyl, heteroarylcarbonyl, oxazolidinyl, isoxazolidinyl, or morpholinyl of $R^{10}$, $R^{11}$, $R_a$–$R_e$, or $R_g$–$R_h$, may optionally be substituted with 1, 2, or 3 Z; and each Z is independently halo, nitro, cyano, hydroxy, $(C_1-C_{10})$alkyl, $(C_3-C_8)$cycloalkyl, $(C_1-C_{10})$alkoxy, $(C_1-C_{10})$alkanoyl, $(C_2-C_{10})$alkanoyloxy, trifluoromethyl, aryl, aryloxy, heteroaryl, or —SR$_f$, wherein $R_f$ is hydrogen, $(C_1-C_{10})$alkyl, $(C_3-C_8)$cycloalkyl, aryl, benzyl, phenethyl, or heteroaryl;

and further wherein any aryl, aryloxy, heteroaryl, benzyl, or phenethyl of Z may optionally be substituted with 1, 2, or 3 substituents independently selected from the group consisting of halo, nitro, cyano, hydroxy, $(C_1-C_{10})$alkyl, $(C_3-C_8)$cycloalkyl, $(C_1-C_{10})$alkoxy, $(C_1-C_{10})$alkanoyl, $(C_2-C_{10})$alkanoyloxy, benzyloxy, 4-methoxybenzyloxy, and trifluoromethyl.

16. The method of claim 15 wherein $R_{10}$ is acetoxymethyl.

17. The method of claim 1 wherein the α-oxo-β-lactam is benzhydryl 6-oxopenicillanate, benzhydryl 7-oxocephalosporanate, or benzhydryl 7-oxo-3'-(desacetoxy)cephalosporanate.

18. The method of claim 2 wherein the α-aminolactam is diazotized by treatment with isopropyl or isoamyl nitrite in the presence of an acid catalyst.

* * * * *

UNITED STATES PATENT AND TRADEMARK OFFICE
CERTIFICATE OF CORRECTION

PATENT NO. : 6,255,479 B1
DATED : July 3, 2001
INVENTOR(S) : Buynak et al.

It is certified that error appears in the above-identified patent and that said Letters Patent is hereby corrected as shown below:

Column 6,
Line 22, delete "c&-oxolactams" and insert -- α-oxolactams --, therefor.

Column 7,
Line 38, delete "iso amyl" and insert -- isoamyl --, therefor.

Signed and Sealed this

Twenty-second Day of January, 2002

Attest:

JAMES E. ROGAN
Attesting Officer
Director of the United States Patent and Trademark Office